United States Patent [19]

Krieger et al.

[11] 4,260,822

[45] Apr. 7, 1981

[54] PROCESS FOR THE PRODUCTION OF UNSATURATED ACIDS

[75] Inventors: Harold Krieger, Philadelphia; Lawrence S. Kirch, Huntingdon Valley, both of Pa.

[73] Assignee: Rohm and Haas Company, Phialdelphia, Pa.

[21] Appl. No.: 956,011

[22] Filed: Oct. 30, 1978

[51] Int. Cl.$^3$ .................... C07C 51/215; C07C 57/05
[52] U.S. Cl. .................................. 562/549; 252/435; 252/437; 562/535; 568/399; 568/475
[58] Field of Search ................. 562/549; 252/435, 437

[56] References Cited

U.S. PATENT DOCUMENTS

| | | | |
|---|---|---|---|
| 3,293,290 | 12/1966 | Flint et al. | 562/549 |
| 4,010,188 | 3/1977 | Grasselli et al. | 562/549 |
| 4,066,704 | 1/1978 | Harris et al. | 562/549 |

*Primary Examiner*—Vivian Garner
*Attorney, Agent, or Firm*—Terence P. Strobaugh; G. W. F. Simmons

[57] ABSTRACT

A process for the direct oxidation of isobutane or propane to methacrylic acid or acrylic acid respectively is disclosed. The process encompasses contacting a feed gas containing isobutane or propane and oxygen with a specific catalyst which is composed of molybdenum, antimony and phosphorus combined with oxygen. The atomic ratio of molybdenum to antimony to phosphorous is from about 9 to about 24; about 0.25 to about 2; and about 0.75 to about 2 respectively. The catalytic oxidation to methacrylic or acrylic acid is accomplished at a temperature of from about 200° C. to about 450° C. The methacrylic or acrylic acid is removed from the feed gases exiting from the reaction zone and the remainder of the exited feed stream may be recycled to again contact the catalyst.

12 Claims, No Drawings

PROCESS FOR THE PRODUCTION OF UNSATURATED ACIDS

BACKGROUND OF THE INVENTION

It is known that methacrylic acid can be produced by the vapor phase oxidation of isobutylene or methacrolein. However, saturated hydrocarbons such as isobutane, are considered inert materials and have often been used as diluents for the reactant gases when preparing unsaturated aldehydes and acids. For example, U.S. Pat. No. 3,293,290, in discussing the prior art, describes the use of low boiling alkanes as inert diluents for reactant gases such as olefins in preparing unsaturated acids.

It is known that methacrylic acid may be prepared from isobutane by direct catalytic oxidation using certain molybdenum and antimony containing catalysts. However, this process suffers from the disadvantage of a very low selectivity when converting the isobutane to methacrylic acid. The selectivity is known to be in the order of about 2% and this factor mitigates against such a process being commercially utilized because of the economics which are involved.

It is an object of this invention therefor to provide a process for the single stage oxidation of isobutane or propane to methacrylic acid or acrylic acid.

Another object of this invention is to provide such a process with a high degree of selectivity for the conversion of the alkane in the feed gas to methacrylic or acrylic acid.

Other objects and advantages will become apparent from the following more complete description and claims.

DETAILED DESCRIPTION

Broadly, this invention contemplates a process for producing methacrylic or acrylic acid comprising the steps of contacting, in the vapor phase and at a temperature of from about 200° C. to about 450° C., an oxygen and alkane containing feed gas wherein said alkane is selected from the class consisting of isobutane and propane, said alkane being present in said feed gas in an amount of from about 10 to about 70 mol. percent with a catalyst comprising $Mo_x$, $Sb_y$ and $P_z$ in combination with oxygen wherein x, y, and z represent the atomic ratio and x is from about 9 to about 24, y is from about 0.25 to about 2, and z is from about 0.75 to about 2 and removing methacrylic or acrylic acid from the contacted feed gas.

The feed gas which is used in practicing the process of this invention contains an alkane (isobutane or propane) in an amount of from about 10 l to about 70 mol. percent and preferably in an amount of from about 10 to about 50 mol. percent e.g., about 20 to about 50 mol. percent. If the isobutane or propane is present in an amount of less than 10 mol. percent, then the efficacy of the process is adversely affected in that the amount of acid formed per unit of reactor volume will be economically low. If however, the feed gas contains isobutane or propane in an amount greater than 70 mol. percent, then such higher amount is undesirable because large amounts of unconverted hydrocarbons will be present in the final gas stream which results from the process. These excessive amounts of unconverted hydrocarbons will increase the complexity of product separation and necessitate recycle of the hydrocarbons in order to have an economically viable process.

The feed gas will contain oxygen. The molar ratio of oxygen to alkane in the feed gas should be between 0.05:1 to about 1:1 and preferably between 0.1:1 to about 0.4:1. Any source of oxygen may be used. From an economic point of view, it is preferred that the source of oxygen be air.

If the molar ratio of oxygen to alkane is less than about 0.05:1, then the economics of the process will be adversely affected in that the amount of oxygen present will be insufficient for the optimum conversion of the alkane to methacrylic or acrylic acid. If however, the molar ratio of oxygen to alkane exceeds about 1:1 then there is the possibility that the oxidation will proceed too far and excessive amounts of carbon dioxide will be formed.

Diluent gases are usually present in the alkane containing feed gas. Although any diluent gas may be used which does not adversely affect the oxidation, it is most convenient to use, as a diluent gas, the nitrogen which is present in air which also serves as the source of supply for the oxygen which is needed for the oxidation of the alkane to methacrylic or acrylic acid.

The catalyst which is used in the process of this invention is important because, it is through this catalyst that the normally inert alkane is able to be oxidized directly, in a single step, to methacrylic or acrylic acid with a high degree of selectivity. It has been found that, using the catalyst set forth below, the oxidation of the alkane, for example isobutane, to methacrylic acid is accomplished with a selectivity as high as 50 percent.

The catalyst used consists of the oxides of antimony, molybdenum and phosphorus. The atomic ratio of the various elements of the catalyst to one another may vary from about 9 to about 24 of molybdenum; about 0.25 to about 2 of antimony; and about 0.5 to about 2 of phosphorus and preferably from about 12 to about 15 of molybdenum; about 1 to about 2 of antimony; and about 1 to about 1.25 of phosphorus. For example, the atomic ratio of molybdenum to antimony to phosphorus may be 12 to 1 to 1 respectively. If the atomic ratio of the various metal oxides are varied beyond those indicated broadly above, then the efficacy of the one step oxidation of alkane, for example isobutane to methacrylic acid, will be adversely affected in that the selectivity of up to about 50 percent will be greatly diminished and will render the process uneconomical.

Although it is not understood why the particular catalyst used is efficacious in the one step conversion of the alkane to methacrylic or acrylic acid, it is possible that the catalyst preparation is responsible for the particular effectiveness of this catalyst.

The catalyst may be prepared by adding antimony pentachloride to a solution containing nitric acid and ammonium hydroxide in deionized water, phosphomolybdic acid is then added to the resultant slurry. The slurry is then stirred with heating for about 16 hours at a temperature of about 50° C. It is thereafter evaporated and dried under vacuum. The solid thereby obtained is then calcined for from about 6 to about 24 hours at a temperature of from about 375° C. to about 425° C. and preferably from about 395° C. to about 405° C. The calcined product is then crushed and particles in the 8 to 30 mesh range are then used.

When water is present in the feed, the selectivity of the alkane to acrylic or methacrylic acid is improved. Generally, the molar ratio of water to alkane should be from about 1:5 to about 5:1. Because water is formed in the course of the reaction, it may not be necessary to add water vapor to the feed gas. It is preferred however that the molar ratio of water to alkane should be from about 1:3 to about 3:1 as excellent results have thereby been obtained.

The pressure at which the reaction is conducted will vary widely from atmospheric pressure to about 5 atmospheres. It is preferred however that the reaction be conducted at a pressure of from about 1 to about 2 atmospheres because the results at such pressure range have been optimal.

The contact time of the feed gas with the catalyst will vary depending upon the desired conversion and the partial pressure of the alkane in the feed gas. Generally, the contact time will be between about 1 and 20 seconds. The contact time may readily be determined by dividing the bulk volume of the catalyst by the volumetric gas flow rate measured at standard temperature and pressure.

The process may be conducted by passing the feed gas over the catalyst for the requisite contact time and at the indicated temperature. It has been found advantageous to pre-heat the feed gas prior to passing such feed gas in contact with the catalyst. After the methacrylic or acrylic acid is removed from the contacted feed gas, the remainder of the gas can be contacted again with the catalyst.

The products of the catalytic oxidation of the alkane are acrylic acid or methacrylic acid, methacrolein or acrolein, carbon monoxide, carbon dioxide, acetic acid and acetone.

The methacrylic or acrylic acid is separated from the other oxidation products and is purified in any suitable manner. Purification of methacrylic or acrylic acid is well known. The methacrolein or acrolein is recycled by combining it with the feed gas which is to be passed in contact with the catalyst. The other products constitute waste products and are removed. If desired, the acetic acid may be recovered as a by-product.

In order to more fully illustrate the nature of this invention and the manner of practicing the same, the following examples are presented.

EXAMPLE 1

Catalyst Preparation 16.4 gms. of antimony pentachloride is added to a solution containing 19.6 gms. of 70 percent nitric acid and 26.5 gms. of 30 percent ammonium hydroxide in 800 gms. of deionized water. 130 gms. of phosphomolybdic acid is then added to the resultant slurry. The slurry is then stirred with heating for 16 hours, whereupon the water is evaporated and the mixture is dried under vacuum. The solid which is thereby obtained is calcined for 6 hours at a temperature of 400° C. The calcined product is then crushed and the particles in the 8 to 30 mesh range are used.

EXAMPLE 2

25 g. of the catalyst prepared above is charged to a fixed bed tubular reactor having 3/8 inch diameter stainless steel tubing. The reactor is then immersed in a molten salt bath to provide heat transfer.

A gaseous mixture containing (mol. percent) 10 percent isobutane, 13 percent oxygen, 48 percent nitrogen and 30 percent steam is passed over the catalyst. The temperature at which the feed gas is passed over the catalyst is 340° C. The reactor pressure is maintained at 20 psig. The contact time of feed gas with catalyst is 6.1 seconds.

10 percent of the isobutane which is fed to the reactor is converted to oxidized products with a 50 percent selectivity to methacrylic acid and a 20 percent selectivity to methacrolein, which is recycled.

EXAMPLE 3

The procedure and equipment of Example 2 is followed.

The gaseous mixture containing (mol. percent) 15% propane, 10% oxygen, 40% nitrogen and 35% steam is passed over 25 grams of the catalyst of Example 1. The contact time of the feed gas with the catalyst is 5.5 seconds. The salt bath temperature is 340° C. and the reactor pressure is 20 psig. p Ten percent of the propane is converted to oxidized products with a 19% selectivity to acrylic acid.

EXAMPLE 4

25 g. of the catalyst of Example 1 is packed into a 3/8 inch diameter tubular reactor of Example 2. The procedure of Example 2 is repeated except that the composition of the feed gas is (mol. percent) 28.4% isobutane, 28.7% molecular oxygen and 42.9% steam. The contact time of feed gas with catalyst is 4.1 seconds. 9% of the isobutane is converted to oxidized products with a 46% selectivity to methacrylic acid and a 10% selectivity to methacrolein.

We claim:

1. A process for producing methacrylic or acrylic acid comprising the steps of contacting in the vapor phase and at a temperature of from about 200° C. to about 450° C., an oxygen and alkane containing feed gas wherein said alkane is selected from the class consisting of isobutane and propane, said alkane being present in said feed gas in an amount of from about 10 to about 70 mol. percent with a catalyst consisting of $Mo_x$, $Sb_y$, and $P_z$ in combination with oxygen wherein x, y and z represent the atomic ratio and x is from about 9 to about 24, y is from about 0.25 to about 2, and z is from about 0.75 to about 2 and removing methacrylic or acrylic acid from the contacted feed gas.

2. A process according to claim 1 wherein, after said methacrylic or acrylic acid is removed from said contacted feed gas, the remainder of the gas is again contacted with said catalyst.

3. A process according to claim 1 wherein the atomic ratio of molybdenum to antimony to phosphorus is 12 to 1 to 1 respectively.

4. A process according to claim 1 wherein the molar ratio of oxygen to alkane in said feed gas is from about 0.05:1 to about 1:1.

5. A process according to claim 4 wherein the molar ratio of oxygen to alkane is from about 0.1:1 to about 0.4:1.

6. A process according to claim 1 wherein water vapor is present in said feed gas.

7. A process according to claim 6 wherein said water vapor is present in an amount so that the molar ratio of water to alkane is from about 1:5 to about 5:1.

8. A process according to claim 1 wherein said feed gas is contacted at a pressure of from about 1 atmosphere to about 5 atmospheres.

9. A process according to claim 1 wherein the contact time of said feed gas with said catalyst is from about 1 to about 20 seconds.

10. A process according to claim 1 wherein said feed gas contains alkane in an amount of from about 20 to about 50 mol. percent.

11. A process according to claim 1 wherein said alkane is isobutane.

12. A process according to claim 1 wherein said alkane is propane.

* * * * *